US008933124B2

(12) United States Patent
Mylari et al.

(10) Patent No.: US 8,933,124 B2
(45) Date of Patent: *Jan. 13, 2015

(54) TRI-SALT FORM OF METFORMIN

(71) Applicant: Thetis Pharmaceuticals LLC, Southport, CT (US)

(72) Inventors: Banavara L. Mylari, Lutz, FL (US); Frank C. Sciavolino, Waterford, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 14/280,015

(22) Filed: May 16, 2014

(65) Prior Publication Data
US 2014/0249221 A1    Sep. 4, 2014

Related U.S. Application Data

(63) Continuation of application No. 13/841,970, filed on Mar. 15, 2013, now Pat. No. 8,765,811.

(60) Provisional application No. 61/669,763, filed on Jul. 10, 2012.

(51) Int. Cl.
A61K 31/205 (2006.01)
C07C 279/02 (2006.01)
C07C 279/26 (2006.01)
C07C 229/24 (2006.01)
C07C 57/03 (2006.01)

(52) U.S. Cl.
CPC ............ A61K 31/205 (2013.01); C07C 279/02 (2013.01); C07C 279/26 (2013.01); C07C 229/24 (2013.01); C07C 57/03 (2013.01)
USPC .......................................... 514/554; 562/571

(58) Field of Classification Search
None
See application file for complete search history.

(56) References Cited

U.S. PATENT DOCUMENTS

| | | | |
|---|---|---|---|
| 5,795,909 A | 8/1998 | Shashoua et al. | |
| 6,372,790 B1 * | 4/2002 | Bonhomme et al. | 514/555 |
| 6,491,950 B1 | 12/2002 | Gutierrez-Rocca et al. | |
| 6,517,870 B1 | 2/2003 | Nishii et al. | |
| 6,602,902 B2 | 8/2003 | Shashoua et al. | |
| 6,667,064 B2 | 12/2003 | Surette | |
| 6,720,001 B2 | 4/2004 | Chen et al. | |
| 6,881,854 B2 | 4/2005 | Ptock et al. | |
| 6,893,627 B2 | 5/2005 | Ribnicky et al. | |
| 7,105,572 B2 | 9/2006 | Sato | |
| 7,195,914 B2 | 3/2007 | Surette | |
| 7,199,151 B2 | 4/2007 | Shashoua et al. | |
| 7,214,387 B2 | 5/2007 | Sanghvi et al. | |
| 7,223,770 B2 | 5/2007 | Zhang et al. | |
| 7,304,089 B2 | 12/2007 | Kramer et al. | |
| 7,429,395 B2 | 9/2008 | Campbell-Tofte | |
| 7,553,870 B2 | 6/2009 | Shibuya | |
| 7,579,025 B2 | 8/2009 | Campbell-Tofte | |
| 7,619,002 B2 | 11/2009 | Shibuya | |
| 7,666,898 B2 | 2/2010 | Chang et al. | |
| 7,670,612 B2 | 3/2010 | Miller | |
| 7,973,073 B2 | 7/2011 | Mylari et al. | |
| 8,058,312 B2 | 11/2011 | Kim et al. | |
| 8,076,377 B2 | 12/2011 | Kim et al. | |
| 2003/0220301 A1 | 11/2003 | Lal et al. | |
| 2005/0158374 A1 | 7/2005 | Wong et al. | |
| 2005/0182029 A1 | 8/2005 | Lal | |
| 2006/0159746 A1 | 7/2006 | Troup et al. | |
| 2006/0229359 A1 | 10/2006 | Zhang et al. | |
| 2006/0240095 A1 | 10/2006 | Junien et al. | |
| 2007/0060532 A1 | 3/2007 | Junien et al. | |
| 2007/0207196 A1 | 9/2007 | Zhang | |
| 2008/0045559 A1 | 2/2008 | Zhang et al. | |
| 2008/0200533 A1 | 8/2008 | Krishnan | |
| 2008/0260819 A1 | 10/2008 | Fleming et al. | |
| 2009/0047340 A1 | 2/2009 | Guilford | |
| 2009/0054513 A1 | 2/2009 | Webster et al. | |
| 2009/0156612 A1 | 6/2009 | Kuroita et al. | |
| 2009/0227560 A1 | 9/2009 | Kuroita et al. | |
| 2010/0035990 A1 | 2/2010 | Bryhn et al. | |
| 2010/0105773 A1 | 4/2010 | Smith et al. | |
| 2010/0121048 A1 | 5/2010 | Kuroita et al. | |
| 2010/0137587 A1 | 6/2010 | Takanobu et al. | |

(Continued)

FOREIGN PATENT DOCUMENTS

WO    WO-03068209 A1    8/2003
WO    WO-2005042539 A1    5/2005

(Continued)

OTHER PUBLICATIONS

Sugiyama et al. in Life Sciences 83 (2008) 19-28.*
"Amino Acid pKa Values" in www.cem.msu.edu/~cem252/sp97/ch24/ch24aa.html, "prandimet-drug" in www.rxlist.com/prandimet-drug.htm (retrieved from the internet Nov. 14, 2013).*
"eicosapentaenoic acid pKa" retrieved from STN Registry File Nov. 14, 2013.*
"Amino Acid Structures." Web. Nov. 14, 2013. http://www.cem.msu.edu/~cem252/sp97/ch24/ch24aa/html.
"Cold Spring Harbor Protocols." 2006. Web. Nov. 13, 2013. http://cshprotocols.cship.org.
"Eicosapentaenoic Acid pKa." STN Registry File. Web. Nov. 14, 2013.
"Prandimet." RxList. Web. Nov. 14, 2013. http://www.rxlist.com/prandimet-drug.htm.
Charles et al. "Treatment with Metformin of Non-Diabetic Men with Hypertension, Hypertriglyceridaemia and Central Fat Distribution: The BIGPRO 1.2 Trial." *Diabetes Metab. Res. Rev.* 16(2000):2-7.

(Continued)

Primary Examiner — Dennis Heyer
(74) Attorney, Agent, or Firm — Mintz Levin Cohn Ferris Glovsky and Popeo, P.C.; Muriel Liberto, Esq.

(57) ABSTRACT

Provided herein are tri-salt compounds comprising a compound having two acidic functional groups and one basic functional groups (e.g., aspartate or glutamate), metformin, and polyunsaturated fatty acids, such as eicosapentaenoate or docosahexaenoate. The salts can be used in the treatment of diabetes, diabetes with concomitant dyslipidemia (e.g., high triglycerides) and diabetes exacerbated cardiovascular complications, such as cardiac arrhythmia, cardiac ischemia, myocardial infarction, cardiomyopathy, and stroke. The compounds of this invention are also useful in treating obesity.

4 Claims, No Drawings

(56) References Cited

U.S. PATENT DOCUMENTS

| | | |
|---|---|---|
| 2010/0324010 A1 | 12/2010 | Imaeda et al. |
| 2011/0046053 A1 | 2/2011 | Kidron |
| 2011/0052678 A1 | 3/2011 | Shantha et al. |
| 2011/0171142 A1 | 7/2011 | Lara |
| 2012/0178813 A1 | 7/2012 | Mylari et al. |
| 2013/0095140 A1 | 4/2013 | Baron et al. |

FOREIGN PATENT DOCUMENTS

| | | |
|---|---|---|
| WO | WO-2005118612 A1 | 12/2005 |
| WO | WO-2009038396 A2 | 3/2009 |
| WO | WO-2010127099 A2 | 11/2010 |

OTHER PUBLICATIONS

Goldberg et al. "Lifestyle and Metformin Treatment Favorably Influence Lipoprotein Subfraction Distribution in the Diabetes Prevention Program." *J. Clin. Endocrinol. Metab.* pub. ahead of print Aug. 26, 2013.

Sugiyama et al. "Eicosapentaenoic Acid Lowers Plasma and Liver Cholesterol Levels in the Presence of Peroxisome Proliferators-Activate Receptor Alpha." *Life Sciences*. 83(2008):1928.

Wulffelé et al. "The Effect of Metformin on Blood Pressure, Plasma Cholesterol and Triglycerides in Type 2 Diabetes Mellitus: A Systematic Review." *J. Intern. Med*. 256.1(2004):1-14.

\* cited by examiner

TRI-SALT FORM OF METFORMIN

RELATED APPLICATION

This application claims priority to U.S. Provisional Application No. 61/669,763, filed Jul. 10, 2012, the contents of which are incorporated herein by reference in its entirety.

BACKGROUND OF THE INVENTION

Diabetes mellitus has become pandemic and according to a forecast by the World Health Organization, there will be a sharp increase in the number of diabetic patients by the year 2030. This is an ominous forecast, because managing the long-term complications of diabetes, which include nephropathy, neuropathy, retinopathy, and cardiovascular complications, will have a serious impact on public health budgets. The hallmark of diabetes is chronically elevated blood glucose levels. It is also known that abnormally elevated glucose levels have an adverse impact on glutathione levels in key diabetic tissues. Furthermore, increased oxidative stress and increased production of reactive oxygen species are implicated under hyperglycemic conditions.

In spite of the early discovery of insulin and its subsequent widespread use in the treatment of diabetes, and the later discovery of and use of sulfonylureas, and thiazolidenediones, such as troglitazone, rosiglitazone or pioglitazone, and DPPIV inhibitors such as sitagliptin as oral hypoglycemic agents, the treatment of diabetes remains less than satisfactory.

The use of insulin requires multiple daily doses, usually by self-injection. Determination of the proper dosage of insulin requires frequent estimations of the sugar in urine or blood. Treatment of non-insulin dependent diabetes mellitus (Type II diabetes, NIDDM) usually consists of a combination of diet, exercise, oral hypoglycemic agents, e.g., thiazolidenediones, and, in more severe cases, insulin. However, the clinically available hypoglycemic agents can either have side effects limiting their use, or an agent may not be effective with a particular patient. In the case of insulin dependent diabetes mellitus (Type I), insulin administration usually constitutes the primary course of therapy.

Accordingly, there remains a need for an effective treatment of diabetes, type 2 diabetes (T2D), and pre-diabetes, as well as related conditions, such as neuropathy, nephropathy, retinopathy, cataracts and cardiovascular complications, including cardiac arrhythmia, myocardial infarction, stroke, and cardiomyopathy in diabetic patients.

SUMMARY OF THE INVENTION

Provided herein are tri-salt compounds comprising aspartate, glutamate, or homologues thereof, metformin, and polyunsaturated fatty acids, such as eicosapentaenoate or docosahexaenoate. The tri-salt compounds can be used in the treatment of diabetes, diabetes with concomitant dyslipidemia (e.g., high triglycerides) and diabetes exacerbated cardiovascular complications, such as cardiac arrhythmia, cardiac ischemia, myocardial infarction, cardiomyopathy, and stroke. The tri-salt compounds are also useful in treating obesity.

Provided herein are tri-salts of a compound with two acidic functional groups and one basic functional group, metformin, and a polyunsaturated fatty acid, which are represented by the following Formula I:

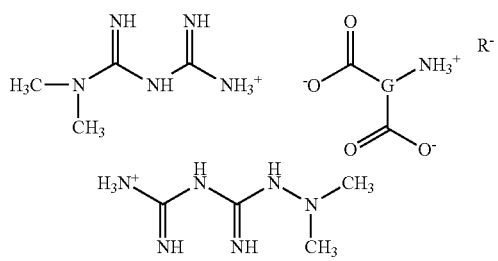

wherein G is an alkyl, cycloalkyl, heteroalkyl, heterocyclyl, aryl, or heteroaryl group; and $R^-$ is a polyunsaturated fatty acid. In an embodiment of Formula I, G is alkyl.

In a particular embodiment, compounds of Formula I are of the Formula II:

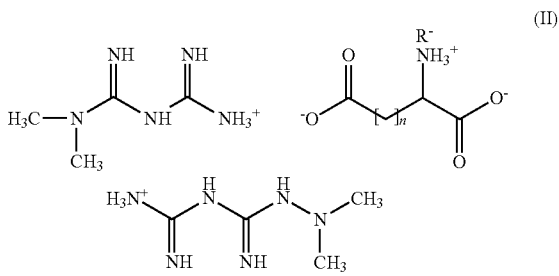

wherein $R^-$ is a polyunsaturated fatty acid, and n is 1-10, or a pharmaceutically acceptable solvate or hydrate thereof. In a particular embodiment of Formula II, n is 1 or 2. In another particular embodiment, n is 3, 4 or 5.

In an embodiment of Formulas I and II, W is eicosapentaenoate or docosahexaenoate. In an embodiment of Formula II, $R^-$ is eicosapentaenoate or docosahexaenoate, and n is 1. In still another embodiment of Formula II, $R^-$ is eicosapentaenoate or docosahexaenoate, and n is 2.

Also provided herein is a pharmaceutical composition comprising a compound of Formula I, and a pharmaceutically acceptable carrier, vehicle or diluent.

Also provided herein is a kit comprising a unit dosage comprising a compound of the invention with instructions on how to use the kit and at least one container for holding the unit dosage form.

The compounds of Formula I can be used in the treatment of a number of diseases and indications. Accordingly, in one aspect, provided herein is a method for treating diabetes in a subject in need thereof, comprising administering to the subject a therapeutically effective amount of a compound of Formula I. In another aspect, provided herein is a method of lowering triglycerides in a subject in need thereof, comprising administering to the subject a therapeutically effective amount of a compound of Formula I. In still another aspect, provided herein is a method for treating cardiovascular diseases in a subject in need thereof, comprising administering to the subject a therapeutically effective amount a compound of Formula I. Examples of cardiovascular diseases to be treated are cardiac arrhythmia, cardiac ischemia, myocardial infarction, cardiomyopathy, or stroke.

In another aspect, provided herein is a method for treating obesity in a subject in need thereof, comprising administering to the subject a therapeutically effective amount of a compound of Formula I.

In one aspect, provided herein is a method of treating hyperlipidemia, comprising administering to a subject in need thereof an effective amount of Formula I. In another aspect, provided herein is a method of treating hypertriglycreridemia, comprising administering to a subject in need thereof an effective amount of a compound of Formula I. In another aspect, provided herein is a method of treating dyslipidemia, comprising administering to a subject in need thereof an effective amount of a compound of the invention. In another aspect, provided herein is a method of treating dyslipidemia, comprising administering to a subject in need thereof an effective amount of a compound of Formula I.

In another aspect, provided herein is a method of treating prediabetes, comprising administering to a subject in need thereof an effective amount of a compound of the invention.

In still another aspect, provided herein is a method of treating atherosclerosis, comprising administering to a subject in need thereof an effective amount of a compound of the invention.

Also provided herein are methods of making the compounds of Formula II. In one aspect, provided herein is a method for the manufacture of a compound of Formula II, wherein R$^-$ is eicosapentaenoate and n is 1, comprising: a) preparing the free base of metformin from a metformin salt; and b) reacting two equivalents of the free base of metformin with one equivalent of aspartic acid one equivalent of eicosapentaenoic acid at a temperature between about 1° C. and about 60° C.

In another aspect, provided herein is a method for the manufacture of a compound of Formula II, wherein R$^-$ is eicosapentaenoate and n is 2, comprising: a) preparing the free base of metformin from a metformin salt; and b) reacting two equivalents of free base of metformin with one equivalent of glutamic acid one equivalent of eicosapentaenoic acid at a temperature between about 1° C. and about 60° C.

In another aspect, provided herein is a method for the manufacture of a compound of Formula II, wherein R$^-$ is docosahexaenoate and n is 1, comprising: a) preparing the free base of metformin from a metformin salt; and b) reacting two equivalents of the free base of metformin with one equivalent of aspartic acid one equivalent of eicosapentaenoic acid at a temperature between about 1° C. and about 60° C.

In yet another aspect, provided herein is a a method for the manufacture of a compound of Formula II, wherein R$^-$ is docosahexaenoate and n is 2, comprising: a) preparing the free base of metformin from a metformin salt; and b) reacting two equivalents of free base of metformin with one equivalent of glutamic acid one equivalent of eicosapentaenoic acid at a temperature between about 1° C. and about 60° C.

DETAILED DESCRIPTION OF THE INVENTION

Metabolic syndrome is intricately intertwined with T2D, which has become pandemic. Clinical presentation of this syndrome is patient-dependent and the co-morbidities in patients with diabetes (chronic hyperglycemia) include high blood pressure, hyperlipidemia and cardiovascular complications, including stroke, myocardial ischemia and cardiomyopathy. The long-term consequences of these co-morbidities also include diabetic nephropathy, diabetic neuropathy, diabetic retinopathy and diabetic cataracts.

Metformin is a known compound approved by the U.S. Food & Drug Administration for the therapeutic treatment of diabetes. The compound and its preparation and use are disclosed, for example, in U.S. Pat. No. 3,174,901. Metformin is orally effective in the treatment of type 2 diabetes. Metformin (N,N-dimethylimidodicarbonimidic diamide) is a biguanide, anti-hyperglycemic agent currently marketed in the United States in the form of its hydrochloride salt 1,1-dimethylbiguanide hydrochloride. Metformin hydrochloride can be purchased commercially and it can also be prepared, for example, as disclosed in J. Chem. Soc., 1922, 121, 1790.

According to United Kingdom Prospective Diabetes Study (UKPDS) (Clarke et al. Diabetologia, 2005, 48, 868-877), metformin therapy was cost-saving and increased quality-adjusted life expectancy. In the UKPDS, overweight and obese patients randomized to initial therapy with metformin experienced significant reductions in myocardial infarction and diabetes-related deaths. Metformin does not promote weight gain and has beneficial effects on several cardiovascular risk factors. Accordingly, metformin is widely regarded as the drug of choice for most patients with Type 2 diabetes. However, even diabetic patients on metformin therapy face the risk of long-term cardiovascular complications such as cardiac arrhythmia, cardiac ischemia, myocardial infarction, cardiomyopathy and stroke. It is thought that elevated triglycerides (TGs) may be an important common biochemical link underpinning the cardiovascular complications.

Epidemiological and clinical evidence suggests that an increased intake of co-3 polyunsaturated fatty acids (PUFAs) protects against mortality from coronary artery diseases. PUFAs include eicosapentaenoic acid (EPA) and docosahexaenoic acid (DHA). It is widely established that PUFAs protect against and can terminate ischemic ventricular arrhythmias (Billman et al. Circulation. 1999, 99, 2452-2457 and Kang et al. Am. J. Clin. Nutr. 2002, 71, 202S-207S). In particular, it is known that EPA is a promising treatment for prevention of major coronary events. PUFAs have multiple biological functions through lipid-dependent and lipid-independent mechanisms. EPA and mixtures of EPA and DHA have been shown to ameliorate triglycerides (TGs) lipid levels in patients with very high TGs. Also, EPA is shown to increase adiponectin secretion both in obese animals and obese human subjects (Itoh et al. Arteroscler. Thromb. Vasc. Biol. 2007, 27, 1918-1925). Increased adiponectin levels are beneficial in regulating both lipid and glucose metabolism in animals as well as in humans. It is also known that many patients with type 2 diabetes and with a prediabetic condition known as metabolic syndrome, sometimes referred to as insulin resistance, suffer from a variety of glucose and lipid metabolism disorders including elevated blood glucose and triglycerides. Accordingly, provided herein are compounds of Formula I, as well as methods for treating diabetes, diabetes with concomitant dyslipidemia (e.g., high triglycerides) and diabetes exacerbated cardiovascular complications, such as cardiac arrhythmia, cardiac ischemia, myocardial infarction, cardiomyopathy, and stroke, comprising administering to a subject in need thereof a compound of Formula I. Compounds of Formula I are also useful in treating obesity in a subject in need thereof.

Compounds of Formula I are tri-salts of a compound having two acidic and one basic functional groups, metformin, and a polyunsaturated fatty acid, and are represented by the following formula:

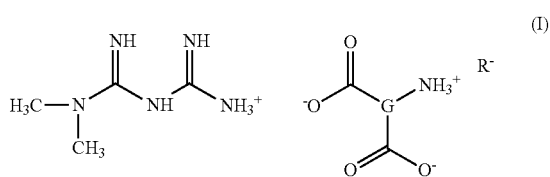

(I)

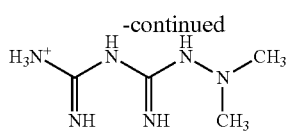

wherein G is an alkyl, cycloalkyl, heteroalkyl, heterocyclyl, aryl, or heteroaryl group; and R⁻ is a polyunsaturated fatty acid. In an embodiment of Formula I, G is alkyl. When G is alkyl, G can be alkylene, e.g., $CH_2$, $CH_2CH_2$, $CH_2CH_2CH_2$, $CH_2CH_2CH_2CH_2$, $CH_2CH_2CH_2CH_2CH_2$, etc., wherein one of the hydrogens is replaced with $NH_3+$.

In one embodiment, compounds of Formula I are represented by the Formula II:

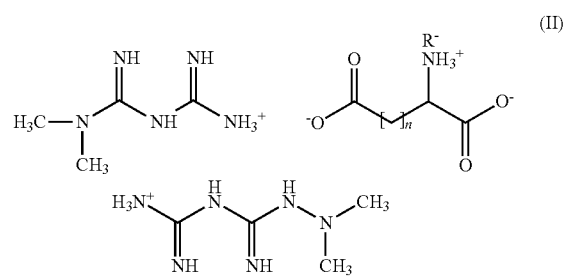

(II)

wherein n is 1-10, and R⁻ is a polyunsaturated fatty acid. In a particular embodiment of Formula II, n is 1-2. In another particular embodiment of Formula II, n is 3-5.

In an embodiment of Formula II, R⁻ is eicosapentaenoate:

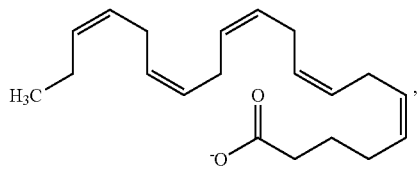

or
docosahexaenoate:

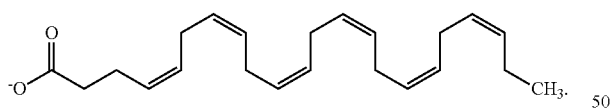

In one embodiment of Formula II, R⁻ is eicosapentaenoate, and n is 1. In another embodiment of Formula II, R⁻ is eicosapentaenoate and n is 2.

In another embodiment of Formula II, R⁻ is docosahexaenoate and n is 1. In another embodiment of Formula II, R⁻ is docosahexaenoate and n is 2.

In certain embodiments, the compound of Formula II is selected from the group consisting of:

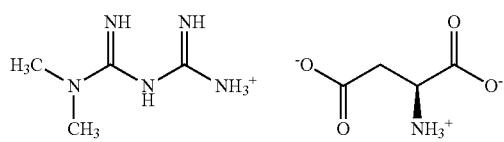

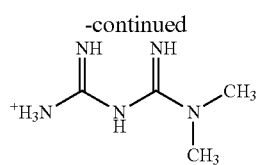

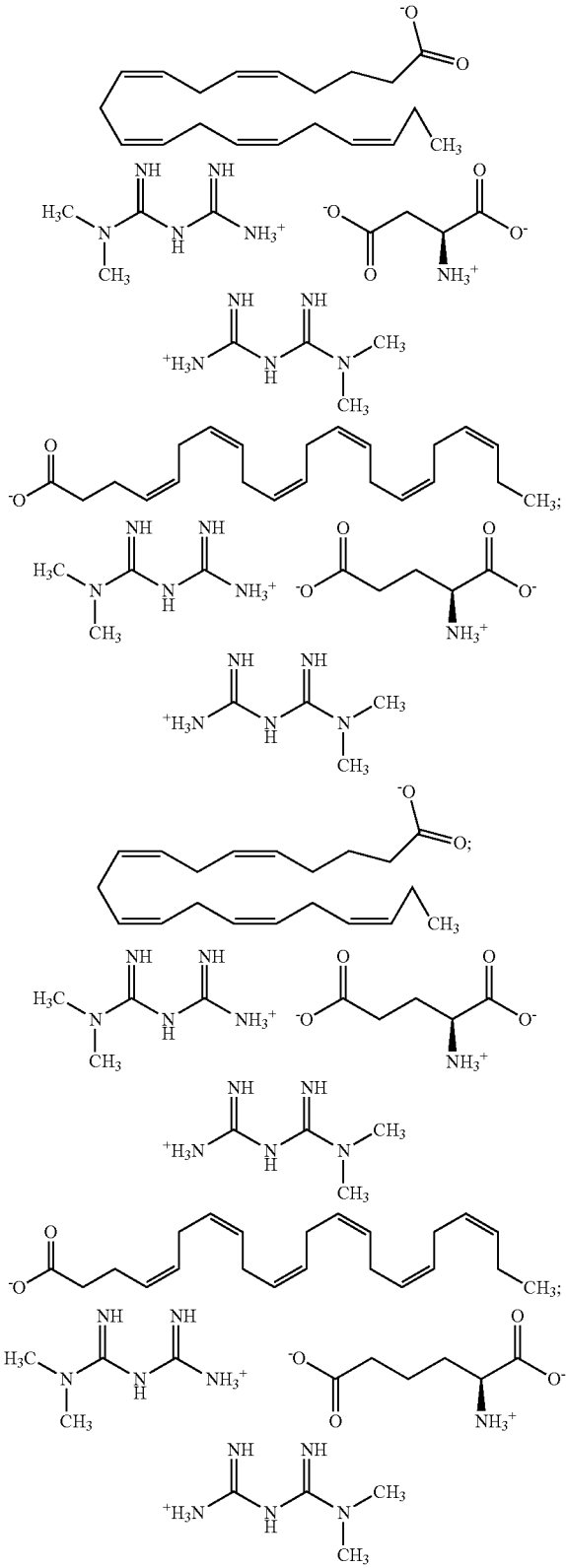

-continued

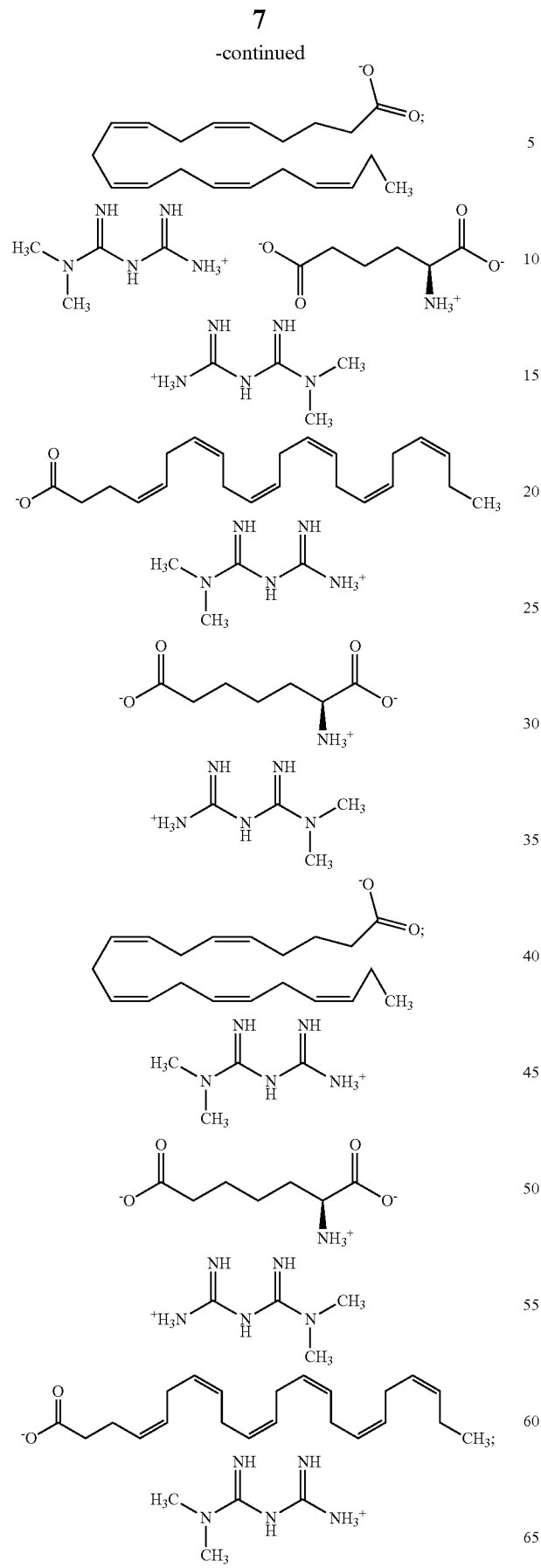

-continued

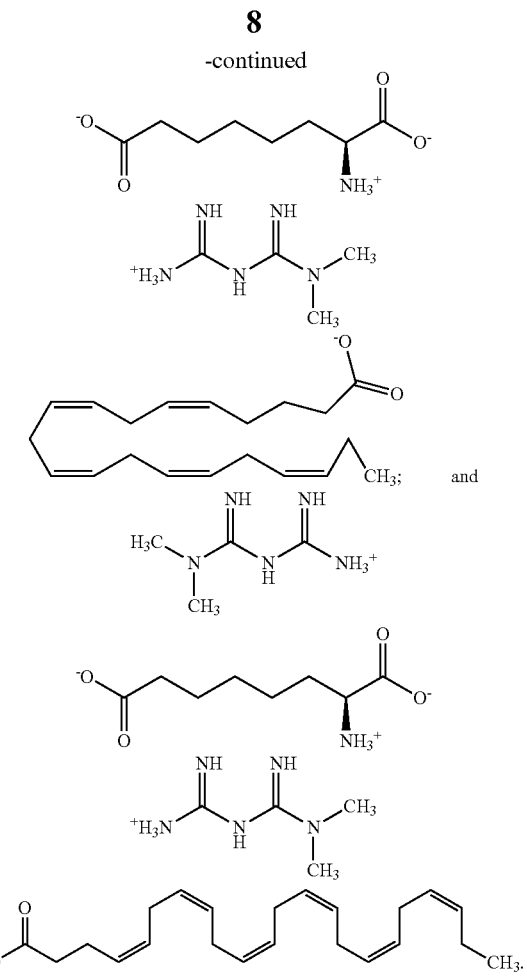

The compounds of Formula I also include isomers and enantiomers wherever it is applicable.

It is well known in the art that highly water soluble medicinal preparations, when administered orally, result in efficient absorption of such preparations from the gastrointestinal tract into systemic circulation. Another hallmark of such preparations is the rate at which they are absorbed into systemic circulation resulting in high concentration of the active agent or agents in the blood. Moreover, for delivery of xenobiotics via the intravenous route, they must be presented as a clear solution. PUFAs and esters of PUFAs are practically insoluble in water. In fact, they form soap-like emulsions when mixed with water. Therefore, the potential to achieve optimum therapeutic benefits of PUFAs should be markedly facilitated by delivery of water soluble PUFAs. The compounds of the present invention are markedly more water soluble than PUFAs and esters of PUFAs to achieve high oral absorption and to provide concomitant delivery of both metformin and PUFAS, thus providing a dual action in targeting both elevated blood glucose levels and TGs prevalent in type 2 diabetes in patients. Furthermore, the new salts would offer a patient friendly dosage form of two active therapies in a fixed dosage combination with increased reliability for daily patient compliance. Juvisync, recently approved by the United States Food and Drug Administration, is a contemporary example of a fixed combination of two widely used drugs for reliability of usage and patient convenience (FDA News Release. Oct. 7, 2011). Furthermore, the compounds of the present invention enable the preparation of intravenous dosage forms.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 7 carbon atoms, 1 to 6 carbons, 1 to 4 carbons, or 1 to 3 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. As used herein, the term "alkyl" also includes "alkenyl" and "alkynyl" groups.

The term "alkenyl," alone or in combination refers to a straight-chain, cyclic or branched hydrocarbon residue comprising at least one olefinic bond and the indicated number of carbon atoms. Preferred alkenyl groups have up to 8, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl, isobutenyl, 1-cyclohexenyl, 1-cyclopentenyl.

The term "alkynyl" includes unsaturated aliphatic groups analogous in length to the alkyls described above, but which contain at least one triple bond. For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

As used herein, the term "cycloalkyl" refers to saturated or unsaturated monocyclic, bicyclic or tricyclic hydrocarbon groups of 3-12 carbon atoms, preferably 3-9, or 3-7 carbon atoms. Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo [2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adarnantyl and the like. As used herein, "cyclo alkyl" includes "cycloalkenyl" groups.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group.

The term "heteroalkyl," by itself or in combination with another term, means, unless otherwise stated, a stable straight or branched chain, or combinations thereof, consisting of the stated number of carbon atoms and from one to five heteroatoms, more preferably from one to three heteroatoms, selected from the group consisting of O, N, Si and S, and wherein the nitrogen and sulfur atoms may optionally be oxidized and the nitrogen heteroatom may optionally be quaternized. The heteroalkyl group is attached to the remainder of the molecule through a carbon atom or a heteroatom.

The term "aryl" includes aromatic monocyclic or multicyclic e.g., tricyclic, bicyclic, hydrocarbon ring systems consisting only of hydrogen and carbon and containing from six to nineteen carbon atoms, or six to ten carbon atoms, where the ring systems may be partially saturated. Aryl groups include, but are not limited to, groups such as phenyl, tolyl, xylyl, anthryl, naphthyl and phenanthryl. Aryl groups can also be fused or bridged with alicyclic or heterocyclic rings which are not aromatic so as to form a polycycle (e.g., tetralin).

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" refers to a five-member to ten-member, fully saturated or partially unsaturated nonaromatic heterocyclic groups containing at least one heteroatom such as O, S or N. The most frequent examples are piperidinyl, morpholinyl, piperazinyl, pyrrolidinyl or pirazinyl. Attachment of a heterocyclyl substituent can occur via a carbon atom or via a hetero atom.

Moreover, the alkyl, heteroalkyl, cycloalkyl, aryl, heteroaryl, and heterocycle groups described above can be "unsubstituted" or "substituted." The term "substituted" is intended to describe moieties having substituents replacing a hydrogen on one or more atoms, e.g., C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2$(halogen), $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}CHO$, $(CR'R'')_{0-3}O(CR'R'')_{0-3}H$, $(CR'R'')_{0-3}S(O)_{0-3}R'$ (e.g., —$SO_3H$, —$OSO_3H$), $(CR'R'')_{0-3}O(CR'R'')_{0-3}H$ (e.g., —$CH_2OCH_3$ and —$OCH_3$), $(CR'R'')_{0-3}S(CR'R'')_{0-3}H$ (e.g., —SH and —$SCH_3$), $(CR'R'')_{0-3}OH$ (e.g., —OH), $(CR'R'')_{0-3}COR'$, $(CR'R'')_{0-3}$ (substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group.

Methods of Treatment

Provided herein is tri-salt having the Formula I. This compound is effective for the treatment of T2D, pre-diabetes, obesity, metabolic syndrome, hypertriglyceridemia and T2D complications such as neuropathy, nephropathy, retinopathy, cataracts and cardiovascular complications, including cardiac arrhythmia, myocardial infarction, stroke, and cardiomyopathy in diabetic patients.

Diabetes mellitus, commonly called diabetes, refers to a disease process derived from multiple causative factors and characterized by elevated levels of plasma glucose, referred to as hyperglycemia. See, e.g., LeRoith, D, et al., (eds.), Diabetes Mellitus (Lippincott-Raven Publishers, Philadelphia, Pa. U.S.A. 1996). Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

The term "obesity" is defined as the condition wherein the individual has a BMI equal to or greater than 30 kg/m$^2$. According to a WHO definition the term obesity may be categorized as follows: the term "class I obesity" is the condition wherein the BMI is equal to or greater than 30 kg/m$^2$ but lower than 35 kg/m$^2$; the term "class II obesity" is the condition wherein the BMI is equal to or greater than 35 kg/m$^2$ but lower than 40 kg/m$^2$; the term "class III obesity" is the condition wherein the BMI is equal to or greater than 40 kg/m$^2$.

The term "euglycemia" is defined as the condition in which a subject has a fasting blood glucose concentration within the normal range, greater than 70 mg/dL (3.89 mmol/L) and less than 100 mg/dL (5.6 mmol/L). The word "fasting" has the usual meaning as a medical term.

The term "hyperglycemia" is defined as the condition in which a subject has a fasting blood glucose concentration above the normal range, greater than 100 mg/dL (5.6 mmol/L). The word "fasting" has the usual meaning as a medical term.

The term "impaired glucose tolerance" or "IGT" is defined as the condition in which a subject has a 2 hour postprandial blood glucose or serum glucose concentration greater than 140 mg/di (7.78 mmol/L) and less than 200 mg/dL (11.11 mmol/L). The abnormal glucose tolerance, i.e. the 2 hour postprandial blood glucose or serum glucose concentration can be measured as the blood sugar level in mg of glucose per dL of plasma 2 hours after taking 75 g of glucose after a fast. A subject with "normal glucose tolerance" has a 2 hour postprandial blood glucose or serum glucose concentration smaller than 140 mg/dL (7.78 mmol/L).

The term "hyperinsulinemia" is defined as the condition in which a subject with insulin resistance, with or without euglycemia, has fasting or postprandial serum or plasma insulin concentration elevated above that of normal, lean individuals without insulin resistance, having a waist-tohip ratio<1.0 (for men) or <0.8 (for women).

The terms "insulin-sensitizing", "insulin resistance-improving" or "insulin resistance-lowering" are synonymous and used interchangeably.

The term "insulin resistance" is defined as a state in which circulating insulin levels in excess of the normal response to a glucose load are required to maintain the euglycemic state (Ford E S, et al. JAMA. (2002) 287:356-9). A method of determining insulin resistance is the euglycaemichyperinsulinaemic clamp test. The ratio of insulin to glucose is determined within the scope of a combined insulin-glucose infusion technique. There is found to be insulin resistance if the glucose absorption is below the 25th percentile of the background population investigated (WHO definition). Rather less laborious than the clamp test are so called minimal models in which, during an intravenous glucose tolerance test, the insulin and glucose concentrations in the blood are measured at fixed time intervals and from these the insulin resistance is calculated. With this method, it is not possible to distinguish between hepatic and peripheral insulin resistance. Furthermore, insulin resistance, the response of a patient with insulin resistance to therapy, insulin sensitivity and hyperinsulinemia may be quantified by assessing the "homeostasis model assessment to insulin resistance (HOMA-IR)" score, a reliable indicator of insulin resistance (Katsuki A, et al. Diabetes Care 2001; 24: 362-5). Further reference is made to methods for the determination of the HOMA-index for insulin sensitivity (Matthews et al., *Diabetologia* 1985, 28:412-19), of the ratio of intact proinsulin to insulin (Forst et al., *Diabetes* 2003, 52(Supp1.1): A459) and to an euglycemic clamp study. In addition, plasma adiponectin levels can be monitored as a potential surrogate of insulin sensitivity. The estimate of insulin resistance by the homeostasis assessment model (HOMA)-IR score is calculated with the formula (Galvin P, et al. Diabet Med 1992; 9:921-8):HOMA-IR=[fasting serum insulin(uU/mUx [fasting plasma glueose(nunol/L)/22.5]

As a rule, other parameters are used in everyday clinical practice to assess insulin resistance. Preferably, the patient's triglyceride concentration is used, for example, as increased triglyceride levels correlate significantly with the presence of insulin resistance.

The "metabolic syndrome", also called "syndrome X" (when used in the context of a metabolic disorder), also called the "dysmetabolic syndrome" is a syndrome complex with the cardinal feature being insulin resistance (Laaksonen D E, et al. *Am J Epidemiol* 2002; 156:1070-7). According to the ATP III/NCEP guidelines (Executive Summary of the Third Report of the National Cholesterol Education Program (NCEP) Expert Panel on Detection, Evaluation, and Treatment of High Blood Cholesterol in Adults (Adult Treatment Panel III) *JAMA: Journal of the American Medical Association* (2001) 285:2486-2497), diagnosis of the metabolic syndrome is made when three or more of the following risk factors are present:

1. Abdominal obesity, defined as waist circumference>40 inches or 102 cm in men, and >35 inches or 94 cm in women; or with regard to a Japanese ethnicity or Japanese patients defined as waist circumference85 cm in men and 90 cm in women;
2. Triglycerides: ⁻150 mg/dL
3. HDL-cholesterol<40 mg/dL in men
4. Blood pressure130/85 mm Hg (SBP130 or DBP85)
5. Fasting blood glucose ⁻100 mg/dL Patients with a predisposition for the development of IGT or IFG or T2D are those having euglycemia with hyperinsulinemia and are by definition, insulin resistant. A typical patient with insulin resistance is usually overweight or obese. If insulin resistance can be detected, this is a particularly strong indication of the presence of pre-diabetes.

Thus, it may be that in order to maintain glucose homoeostasis a person needs 2-3 times as much insulin as a healthy person, without this resulting in any clinical symptoms.

The methods to investigate the function of pancreatic beta-cells are similar to the above methods with regard to insulin sensitivity, hyperinsulinemia or insulin resistance: An improvement of beta-cell function can be measured for example by determining a HOMA-index for beta-cell function (Matthews et al., *Diabetologia* 1985, 28:412-19), the ratio of intact proinsulin to insulin (Forst et al., *Diabetes* 2003, 52(Suppl.1): A459), the insulin/C-peptide secretion after an oral glucose tolerance test or a meal tolerance test, or by employing a hyperglycemic clamp study and/or minimal modeling after a frequently sampled intravenous glucose tolerance test (Stumvoll et al., *Eur Clin Invest* 2001, 31: 38081).

"Pre-diabetes" is the condition wherein an individual is pre-disposed to the development of type 2 diabetes. Pre-diabetes extends the definition of impaired glucose tolerance to include individuals with a fasting blood glucose within the high normal range 100 mg/dL (J. B. Meigs, et al. Diabetes 2003; 52:1475-1484) and fasting hyperinsulinemia (elevated plasma insulin concentration). The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749).

Individuals likely to have insulin resistance are those who have two or more of the following attributes: 1) overweight or obese, 2) high blood pressure, 3) hyperlipidemia, 4) one or more 1 degree relative with a diagnosis of IGT or IFG or type 2 diabetes. Insulin resistance can be confirmed in these individuals by calculating the HOMA-IR score. For the purpose of this invention, insulin resistance is defined as the clinical condition in which an individual has a HOMA-IR score>4.0 or a HOMA-IR score above the upper limit of normal as defined for the laboratory performing the glucose and insulin assays.

The term "type 2 diabetes" is defined as the condition in which a subject has a fasting blood glucose or serum glucose concentration greater than 125 mg/dL (6.94 mmol/L). The measurement of blood glucose values is a standard procedure in routine medical analysis. If a glucose tolerance test is carried out, the blood sugar level of a diabetic will be in excess of 200 mg of glucose per dL (11.1 mmol/l) of plasma 2 hours after 75 g of glucose have been taken on an empty stomach. In a glucose tolerance test 75 g of glucose are administered orally to the patient being tested after 10-12 hours of fasting and the blood sugar level is recorded immediately before taking the glucose and 1 and 2 hours after taking it. In a healthy subject, the blood sugar level before taking the glucose will be between 60 and 110 mg per dL of plasma, less than 200 mg per dL 1 hour after taking the glucose and less than 140 mg per dL after 2 hours. If after 2 hours the value is between 140 and 200 mg, this is regarded as abnormal glucose tolerance.

The term "late stage T2D mellitus" includes patients with a secondary drug failure, indication for insulin therapy and progression to micro- and macrovascular complications e.g. diabetic nephropathy, or coronary heart disease (CHD)

The methods, compositions, and kits of the invention are useful in treating diabetic complications, including, but not limited to, diabetic neuropathy, diabetic nephropathy, diabetic cardiomyopathy, myocardial infarction, cataracts and diabetic retinopathy.

The term "treating," as used herein, refers to retarding, arresting or reversing the progress of, or alleviating or preventing either the disorder or condition to which the term "treating", applies, or one or more symptoms of such disorder or condition.

The term "treatment," as used herein, refers to the act of treating a disorder, symptom or condition, as the term "treating," is defined above.

The triglyceride lowering efficacy of the compounds of the present invention can be determined in animal models according to the procedure described by Sidika et al in Journal of Lipid Research, 1992, 33, 1-7.

In still another aspect, provided herein is a method of treating atherosclerosis, comprising administering to a subject in need thereof an effective amount of a compound of the invention. Atherosclerosis refers to the buildup of fats and cholesterol in and on artery walls (plaques), which can restrict blood flow. These plaques can also burst, triggering a blood clot. Although atherosclerosis is often considered a heart problem, it can affect arteries anywhere in the body. An animal model of atherosclerosis research is described in *Laboratory Animals* (2004) 38, 246-256.

In another embodiment, compounds of Formula I (e.g., compounds of Formula II) can be administered in combination with additional forms of metformin. For example, compounds of Formula I can be administered to a subject in combination with metformin docosahexaenoate, metformin eicosapentaenoate, or a mixture thereof. In another embodiment, compounds of Formula I can be administered in combination with a non-fatty acid salt form of metformin, e.g., metformin hydrochloride, succinate, or fumarate, or in combination with the free base of metformin. Metformin hydrochloride can be purchased commercially and can also be prepared, for example, as disclosed in J. Chem. Soc., 1922, 121, 1790.

In addition, compounds of Formula I can be administered in combination with eicosapentanoic acid, and/or docosahexaenoic acid.

Pharmaceutical Compositions

The tri-salts of the present invention are suitable as active agents in pharmaceutical compositions that are efficacious particularly for treating diabetes, obesity, and related conditions. The pharmaceutical composition in various embodiments has a pharmaceutically effective amount of the present active agent along with other pharmaceutically acceptable excipients, carriers, fillers, diluents and the like. Pharmaceutical compositions suitable for the delivery of compounds of the present invention and methods for their preparation will be readily apparent to those skilled in the art. Such compositions and methods for their preparation may be found, for example, in 'Remington's. Pharmaceutical Sciences', 19th Edition (Mack Publishing Company, 1995).

The language "pharmaceutical composition" includes preparations suitable for administration to mammals, e.g., humans. When the compounds of the present invention are administered as pharmaceuticals to mammals, e.g., humans, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" is art recognized and includes a pharmaceutically acceptable material, composition or vehicle, suitable for administering compounds of the present invention to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, buccal, sublingual, rectal, vaginal and/or parenteral administration. The formulations may conveniently be presented in unit dosage form and may be prepared by any methods well known in the art of pharmacy. The amount of active ingredient that can be combined with a carrier material to produce a single dosage form will generally be that amount of the compound that produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Dosage

For administration to human patients, the total daily dose of the compounds of the invention is typically in the range of 0.25 g-6 g, 0.25 g-4 g, 0.25 g-2 g, or 0.25 g-1 g, depending, of course, on the mode of administration. In one embodiment the total daily dose is in the range 1 g to 10 g and in another embodiment the total daily dose is in the range 1 g to 6 g. The total daily dose may be administered in single or divided doses.

These dosages are based on an average human subject having a weight of about 65 kg to 70 kg. The physician will readily be able to determine doses for subjects whose weight falls outside this range, such as infants and the elderly.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Kits

Advantageously, the present invention also provides kits for use by a consumer for treating disease. The kits comprise a) a pharmaceutical composition comprising a tri-salt of the invention and a pharmaceutically acceptable carrier, vehicle or diluent; and, optionally, b) instructions describing a method of using the pharmaceutical composition for treating the specific disease.

A "kit" as used in the instant application includes a container for containing the separate unit dosage forms such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle which is in turn contained within a box.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a written memory aid, where the written memory aid is of the type containing information and/or instructions for the physician, pharmacist or subject, e.g., in the form of numbers next to the tablets or capsules whereby the numbers correspond with the days of the regimen which the tablets or capsules so specified should be ingested or a card which contains the same type of information. Another example of such a memory aid is a calendar printed on the card e.g., as follows "First Week, Monday, Tuesday," . . . etc. . . . "Second Week, Monday, Tuesday, . . . " etc. Other variations of memory aids will be readily apparent. A "daily dose" can be a single tablet or capsule or several tablets or capsules to be taken on a given day.

Another specific embodiment of a kit is a dispenser designed to dispense the daily doses one at a time. Preferably, the dispenser is equipped with a memory-aid, so as to further facilitate compliance with the regimen. An example of such a memory-aid is a mechanical counter, which indicates the number of daily doses that, has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

One embodiment of the present invention relates to a kit comprising a unit dosage comprising a compound of the invention with instructions on how to use the kit and with provision for at least one container for holding the unit dosage form.

Methods of Making

The tri-salts of the invention can be prepared using any number of synthesis techniques known to the skilled artisan.

The compound of Formula II, wherein $R^-$ is eicosapentaenoate and n is 1, can be prepared by reacting one equivalent of aspartic acid with two equivalents of metformin free base followed by one equivalent of EPA. The solvents for conducting the reaction can be alcoholic solvents, such as ethanol, methanol, propanol, and isopropanol, ketonic solvents, such as acetone, ethyl methyl ketone, and methyl isopropyl ketone, acetonitrile. The reaction can conducted at temperature from between 0° C. to reflux temperature in ° C. of the solvent used. The reaction time is determined by completion of reaction as monitored by analytical techniques, such as high pressure liquid chromatography.

The compound of Formula II, wherein $R^-$ is eicosapentaenoate and n is 2, can be prepared according to the procedure described above, except that aspartic acid is replaced by glutamic acid.

The compound of Formula II, wherein $R^-$ is docosahexaenoate and n is 1, can be prepared by reacting one equivalent of aspartic acid with two equivalents of metformin free base followed by one equivalent of DHA. The solvents for conducting the reaction can be alcoholic solvents, such as ethanol, methanol, propanol, and isopropanol, ketonic solvents, such as acetone, ethyl methyl ketone, and methyl isopropyl ketone, acetonitrile. The reaction can conducted at temperature from between 0° C. to reflux temperature in ° C. of the solvent used. The reaction time is determined by completion of reaction as monitored by analytical techniques, such as high pressure liquid chromatography.

The compound of Formula II, wherein $R^-$ is docosahexaenoate and n is 2, can be prepared according to the procedure described above, except that aspartic acid is replaced by glutamic acid.

Animal Models

The following example describes a diabetic rat model that may be used for determination of conditions leading to a method for treatment and prevention of post-ischemic damage of the heart and heart tissue.

Spontaneously diabetic Bio-Bred (BB/W) rats are considered a useful model of autoimmune human insulin-dependent diabetes DM).vLike human IDDM, spontaneous diabetes appears during adolescence, with an abrupt clinical onset characterized by weight loss, hyperglycemia, hypoinsulinemia, and ketonuria. As in the case of human diabetics, pathological changes in retina, myocardium, liver, kidney, bone metabolism and peripheral nerves have all been well documented in BB rats, as described in Diab. Metab.Rev., 8:9 (1992).

Isolated Perfused Heart Model

This example describes an isolated perfused rat heart model used in development of the invention. Studies are performed using an isovolumic isolated rat heart preparation. Acutely diabetic male BB/W rats and non-diabetic age-matched (3 to 4 months old) control are pretreated with heparin (1000 u; IP), followed by sodium pentobarbital (65 mg/kg; IP). After deep anaesthesia is achieved as determined by the absence of a foot reflex, the hearts are rapidly excised and placed into iced saline. The arrested hearts are retrograde perfused in a non-recirculating model through the aorta within 2 minutes following their excision. Left ventricular developed pressure (LVDP) is determined using a latex balloon in the left ventricle with high pressure tubing connected to a pressure transducer. Perfusion pressure is monitored using high pressure tubing off the perfusion line. Hemodynamic measurements are recorded on a 4-channel Gould recorder. The system has two parallel perfusion lines with separate oxygenators, pumps and bubble traps, but common temperature control allows rapid change perfusion media. The hearts are perfused using an accurate roller pump. The perfusate consists of 118 mM NaCl, 0.47 mM KCl, 12 mM $CaCl_2$, 12 mM MgCl2, 25 mM $NaHCO_3$, and the substrate 11 mM glucose. The perfusion apparatus is tightly temperature-controlled, with heated baths being used for the perfusate and for the water jacketing around the perfusion tubing to maintain heart temperature at 37±0.5° C. under all conditions. The oxygenated perfusate in the room temperature reservoir is passed through 25 ft. of thin-walled silicone tubing surrounded by distilled water at 37° C. saturated with 95% oxygen.

The perfusate then enters the water-jacketed (37° C.) tubing leading to the heart through a water jacketed bubble trap. This preparation provides excellent oxygenation that routinely has been stable for 3 to 4 hours.

Model for Zero-/Low Ischemia

This example describes a procedure used for study of zero-flow ischemia in diabetic control, diabetic treated, non-diabetic treated and control isolated hearts. Diabetic control (DC) diabetic treated (DZ) normal (C) control and normal treated (CZ) hearts are subjected to 20 minutes of normoxic perfusion followed by 20 minutes of zero-flow ischemia where the perfusate flow is completely shut off, followed by 60 minutes of reperfusion. Hearts are treated with 10 μM metformin eicosapentaenoate. In the metformin eicosapentaenoate treated diabetic group (DZ), hearts are subjected to 10 minutes of normoxic perfusion with normal Krebs-Henseleit buffer and 10 minutes of normoxic perfusion with Krebs-Henseleit buffer containing 10 μM metformin eicosapentaenoate. The hearts are then subjected to 20 minutes of zero-flow ischemia followed by 60 minutes of reperfusion. In order to avoid any variability in reperfusion conditions, both DC and DZ hearts are reperfused with normal Krebs-Henseleit buffer.

Model for Low-Flow Ischemia

This example describes a procedure used for study of low-flow ischemia in diabetic controls, diabetic treated, non-diabetic treated and non-diabetic control isolated hearts. Diabetic control hearts (DC) are subjected to 20 minutes of normoxic perfusion at a flow rate of 12.5 mL/minute followed by 30 minutes of low-flow ischemia where the perfusate flow is slowed down to 1.25 mL/min, that is about 10% of normal perfusion, followed by 30 minutes of reperfusion at a normal flow rate (12.5 mL/min). In the metformin eicosapentaenoate treated diabetic or non-diabetic groups (DZ or CZ), hearts are subjected to 10 minutes of normoxic perfusion (flow rate 12.5 mL/min) with normal Krebs-Henseleit buffer and 10 minutes of normoxic perfusion with Krebs-Henseleit buffer containing 10 μM metformin eicosapentaenoate. The hearts are subjected to 30 minutes of low-flow ischemia (flow rate 1.25 mL/min) and 30 minutes of reperfusion at normal flow rate (12.5 mL/min).

Animal models to determine the effects of compounds of the invention on diabetes and complications of diabetes have been reviewed by Tirabassi et al., *ILAR Journal,* 2004, 45, 292-302. Antidiabetic activity may also be tested according to protocols described in the following patents: U.S. Pat. Nos. 4,340,605; 4,342,771; 4,367,234; 4,617;312; 4,687,777 and 4,703,052. Additional references relevant to this application include the following: French Patent 2796551 and United States Published Patent Application No. 20030220301.

Example 1

Preparation of Bis[{[dimethylamino)(imino)methl]amino}(imino)methanaminium]2S-2-amininium (5Z,8Z,11Z,14Z,17Z)-icosa-5,8,11,14,17-pentaenoate-pentanedioate(Met2-Glu-EPA)

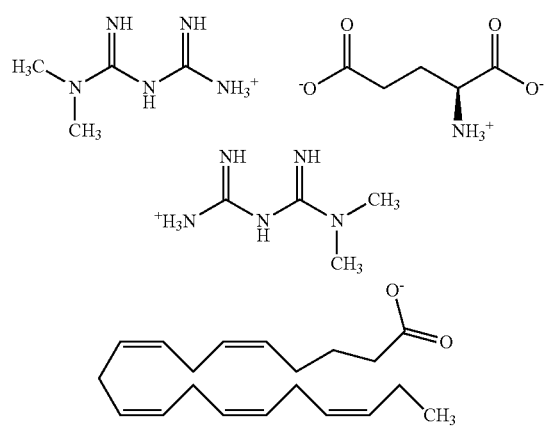

Step 1—Preparation of Bis[{[(dimethylamino)(imino)methyl]amino}(imino)methanaminium](2S)-2-aminopentanedioate

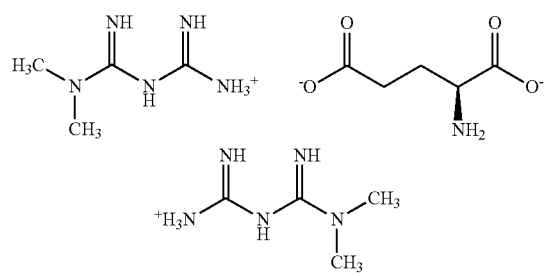

A solution of N,N-dimethylimidodicarbonimidic diamide (1.00 g, 7.74 mmol) in methanol (40 mL) is treated with a solution of L-glutamic acid (0.570 g, 3.87 mmol) in methanol (40 mL) at RT under $N_2$. The mixture is stirred at RT for ½ hr. The methanol is evaporated and the remaining oil is triturated with $CH_3CN$ to give a white solid. The solid is dried at RT under hi-vac for 3 hrs, then stirred in $CH_3CN$ (50 ml) at RT for 2 hrs. The solid is collected by filtration and dried under hi-vac at RT for 1 hr to give 1.3 g of bis[{[(dimethylamino)(imino)methyl]amino}-(imino)methanaminium] (2S)-2-aminopentanedioate as a white solid. $^1$H NMR (300 MHz, MeOD) d 1.88 (m, 1H) 2.06 (m, 2H) 2.30 (m, 2H) 3.05 (s, 12H) 4.91 (s, 14H); MS (ESI–) for $C_5H_9NO_4$ m/z 146 (M–H)$^-$. MS (ESI+) for $C_4H_{11}N_5$ m/z 130 (M+H)$^+$. Anal Calcd for $C_{13}H_3N_{11}O_4$ plus 0.75% $H_2O$: C, 38.22; H, 7.73; N, 37.71. Found: C, 38.57; H, 7.65; N, 36.73.

Step 2—Preparation of Bis[{[(dimethylamino)(imino)methyl]amino}(imino)methanaminium](2S)-2-amininium(5Z,8Z,11Z,14Z,17Z)-icosa-5,8,11,14,17-pentaenoate-pentanedioate (Met2-Glu-EPA)

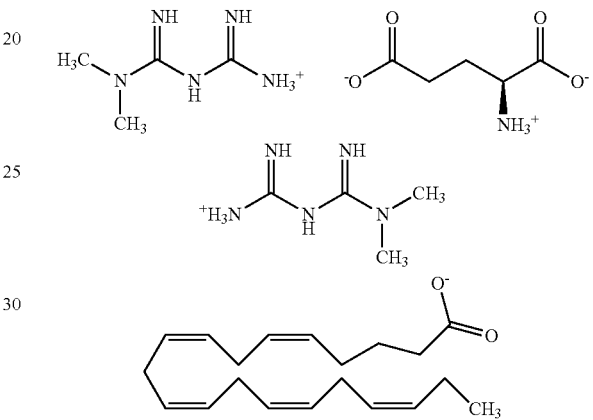

A solution of bis[{[(dimethylamino)(imino)methyl]amino}(imino)methanaminium] (2S)-2-aminopentanedioate (4.28 g, 15.5 mmol) in methanol (180 mL) is stirred with (5Z,8Z,11Z,14Z,17Z)-icosa-5,8,11,14,17-pentaenoic acid (5.15 g, 17.0 mmol) at RT in an amber flask under $N_2$ for 1 hour. The methanol is evaporated and the remaining oil is triturated with ice cold $CH_3CN$ (50 ml) to form a solid. This solid is collected by filtration in the dark and dried at RT in the dark under hi-vac. Yield=10 g of bis[{[(dimethylamino)(imino)methyl]amino}(imino)methanaminium](2S)-2-amininium (5Z,8Z,11Z,14Z,17Z)-icosa-5,8,11,14,17-pentaenoate-pentanedioate as a light tan solid. $^1$H NMR (300 MHz, MeOD) d 0.92 (t, 3H) 1.67 (m, 2H) 2.10 (m, 8H) 2.47 (m, 2H) 2.86 (m, 8H) 3.05 (s, 12H) 3.57 (m, 1H) 4.88 (m, 15H) 5.37 (m, 10H); $C_{20}H_{30}O_2$ m/z 303 (M+H)$^+$; Anal Calcd for $C_{33}H_{61}N_{11}O_6$ plus 1.26% $H_2O$: C, 55.28; H, 8.72; N, 21.49. Found: C, 55.24; H, 8.71; N, 20.81. MP=127-130° C. (Softens@100° C.).

Example 2

Rat Pharmacokinetics of Di-Metformin Glutamate Eicosapentaenoate

Single dose oral pharmacokinetic parameters for di-metformin glutamate eicosapentaenoate, prepared by the procedure described in Example 1, were determined in Sprague-Dawley rats. Di-metformin glutamate eicosapentaenoate was administered by oral gavage as an aqueous solution in 0.5% carboxymethyl cellulose to 6 rats, 3 males and 3 females. Rats were dosed at 52 mg/kg. Blood samples were obtained from each rat by jugular vein catheter. Samples were collected at 0.25, 0.5, 1, 2, 4, 8, 12, and 24 hours post dose. Blood samples were centrifuged to separate red blood cells and the resulting plasma samples were analyzed for eicosapentaenoic acid. Calculated pharmacokinetic parameters shown below in Table 1 are mean values from 6 rats.

TABLE 1

Rat Oral Pharmacokinetic Parameters for Di-metformin glutamate Eicosapentaenoate

| Analyte | EPA | Metformin |
|---|---|---|
| $C_{max}$ (μg/mL) | 14.97 | 2.07 |
| $T_{max}$ (h) | 0.5 | 1.0 |
| AUC (0-24) (μg * h/mL) | 228.67 | 8.49 |

The invention claimed is:

1. A pharmaceutical composition comprising a therapeutically effective amount of a salt of metformin, aspartic acid, and eicosapentaenoate (EPA), and a pharmaceutically acceptable carrier, the salt having the structure of Formula II,

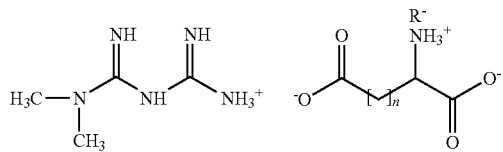

(II)

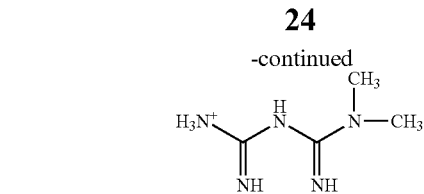

wherein $R^-$ is eicosapentaenoate, and n is 1.

2. A pharmaceutical composition comprising a therapeutically effective amount of a salt of metformin, aspartic acid, and docosahexaenoate (DHA), and a pharmaceutically acceptable carrier, the salt having the structure of Formula II,

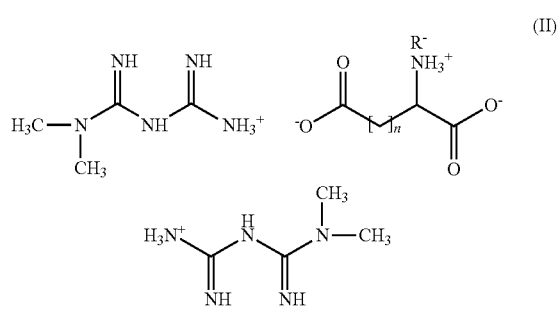

(II)

wherein $R^-$ is docosahexaenoate, and n is 1.

3. A pharmaceutical composition comprising a therapeutically effective amount of the metformin salt of claim 1 or 2.

4. A kit comprising a unit dosage form comprising the pharmaceutical composition of claim 3, instructions for use, and at least one container for holding the unit dosage form.

* * * * *